US012458780B2

(12) United States Patent
Ma et al.

(10) Patent No.: US 12,458,780 B2
(45) Date of Patent: Nov. 4, 2025

(54) INHIBITING FLUID LEAKAGE AND SPLATTER IN CATHETER DEVICES AND SYSTEMS

(71) Applicant: Becton, Dickinson and Company, Franklin Lakes, NJ (US)

(72) Inventors: Yiping Ma, Layton, UT (US); John Stokes, Pleasant View, UT (US); Chad Alan Tagge, Sandy, UT (US); Lawrence J. Trainer, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 355 days.

(21) Appl. No.: 17/113,716

(22) Filed: Dec. 7, 2020

(65) Prior Publication Data

US 2021/0187250 A1 Jun. 24, 2021

Related U.S. Application Data

(60) Provisional application No. 62/949,939, filed on Dec. 18, 2019.

(51) Int. Cl.
*A61M 25/06* (2006.01)

(52) U.S. Cl.
CPC ..... *A61M 25/0618* (2013.01); *A61M 2205/02* (2013.01)

(58) Field of Classification Search
CPC .......... A61M 25/0625; A61M 25/0618; A61M 25/0631; A61M 2005/325; A61B 5/150534
See application file for complete search history.

(56) References Cited

U.S. PATENT DOCUMENTS

| | | | | |
|---|---|---|---|---|
| 5,053,017 A * | 10/1991 | Chamuel | A61M 5/3273 | 604/263 |
| 5,112,311 A * | 5/1992 | Utterberg | A61M 25/0637 | 604/177 |

(Continued)

FOREIGN PATENT DOCUMENTS

| | | |
|---|---|---|
| AR | 057739 A1 | 12/2007 |
| AU | 4703096 A | 8/1996 |

(Continued)

OTHER PUBLICATIONS

Viscoelasticity of PTFE-Based Face Seals, Tan, B. (dissertation submitted in partial fulfillment of the requirements for the degree of Doctor of Philosophy in the College of Engineering at the University of Kentucky, 2021) (orcid.org/0000-0002-7064-865X) (accessed Mar. 17, 2023) (Year: 2021).*

*Primary Examiner* — Bhisma Mehta
*Assistant Examiner* — Adam J. Cermak
(74) *Attorney, Agent, or Firm* — Kirton McConkie; Whitney Blair; Kevin Stinger

(57) ABSTRACT

A needle tip shield may include a needle passageway that may receive a needle, a tip shield interior space that may receive a needle block, and a fluid restriction member. The fluid restriction member may be configured to restrict fluid leakage into and/or out of the needle tip shield. The fluid restriction member may be selected from the group consisting of: (1) a fluid impedance member located adjacent the needle passageway that may impede fluid from entering into the needle tip shield through the needle passageway; (2) a fluid retention member that may retain fluid within the tip shield interior space; and (3) an anti-splatter member that may inhibit fluid splatter when the needle block moves from an open position to a closed position within the tip shield interior space.

4 Claims, 6 Drawing Sheets

(56) References Cited

U.S. PATENT DOCUMENTS

| | | | | | |
|---|---|---|---|---|---|
| 5,584,809 | A * | 12/1996 | Gaba | A61M 25/0618 604/110 |
| 5,601,532 | A | 2/1997 | Gaba | |
| 5,697,907 | A * | 12/1997 | Gaba | A61M 25/0618 604/110 |
| 5,718,688 | A * | 2/1998 | Wozencroft | A61M 25/0618 604/164.07 |
| 5,810,784 | A * | 9/1998 | Tamaro | A61M 5/3275 128/919 |
| 7,740,614 | B2 * | 6/2010 | Murashita | A61M 5/158 604/164.08 |
| 8,585,650 | B2 * | 11/2013 | Carrez | A61M 25/0631 604/164.08 |
| 11,344,704 | B2 * | 5/2022 | Spataro | A61M 25/0102 |
| 2005/0027255 | A1 * | 2/2005 | Lavi | A61M 5/326 604/135 |
| 2007/0038188 | A1 | 2/2007 | Bialecki et al. | |
| 2007/0270754 | A1 * | 11/2007 | Soderholm | A61M 25/0625 604/110 |
| 2008/0065015 | A1 * | 3/2008 | Fiser | A61M 25/0618 604/110 |
| 2008/0243086 | A1 * | 10/2008 | Hager | A61M 25/0625 604/198 |
| 2008/0243092 | A1 * | 10/2008 | Nilsson | A61M 25/0606 604/272 |
| 2009/0082732 | A1 | 3/2009 | Hillman | |
| 2011/0319820 | A1 * | 12/2011 | Teoh | A61M 25/0606 604/122 |
| 2013/0023835 | A1 * | 1/2013 | Kuracina | A61B 5/150633 604/263 |
| 2013/0030370 | A1 * | 1/2013 | Walker | A61M 25/0618 604/164.08 |
| 2015/0051584 | A1 * | 2/2015 | Korkuch | A61M 25/0606 604/95.01 |
| 2015/0335864 | A1 * | 11/2015 | Knutsson | A61M 5/3273 604/263 |
| 2016/0354539 | A1 * | 12/2016 | Tan | A61M 5/158 |
| 2017/0035992 | A1 * | 2/2017 | Harding | A61M 5/3213 |
| 2017/0120017 | A1 | 5/2017 | Burkholz et al. | |
| 2017/0319822 | A1 * | 11/2017 | Ang | A61M 25/0097 |
| 2017/0333642 | A1 * | 11/2017 | Shevgoor | A61M 5/348 |
| 2018/0043093 | A1 * | 2/2018 | Nakagami | A61M 25/0693 |
| 2018/0064885 | A1 * | 3/2018 | Yamazaki | A61M 5/32 |
| 2018/0221592 | A1 * | 8/2018 | Brugger | A61B 5/150885 |
| 2018/0289932 | A1 * | 10/2018 | Isaacson | A61M 25/0618 |
| 2019/0160264 | A1 * | 5/2019 | Isaacson | A61M 5/3243 |
| 2019/0269889 | A1 * | 9/2019 | Ma | A61M 25/0606 |
| 2019/0314615 | A1 * | 10/2019 | Johnson | A61M 25/0606 |
| 2019/0388653 | A1 * | 12/2019 | Breindel | A61M 25/0606 |
| 2020/0222671 | A1 | 7/2020 | Burkholz et al. | |
| 2020/0230367 | A1 * | 7/2020 | Dalena | A61M 25/0631 |
| 2020/0230368 | A1 * | 7/2020 | Breindel | A61M 25/0631 |
| 2020/0338314 | A1 * | 10/2020 | Ebner | A61M 25/0618 |
| 2021/0008348 | A1 | 1/2021 | Isaacson | |
| 2021/0100985 | A1 * | 4/2021 | Akcay | A61M 39/22 |
| 2021/0290913 | A1 * | 9/2021 | Horst | A61M 25/09 |
| 2021/0386974 | A1 * | 12/2021 | Jiang | A61M 39/10 |
| 2022/0000517 | A1 * | 1/2022 | Baid | A61B 17/3403 |
| 2022/0280756 | A1 * | 9/2022 | Woehr | A61M 25/0625 |

FOREIGN PATENT DOCUMENTS

| | | | | |
|---|---|---|---|---|
| AU | 2008304568 A1 | 4/2009 | |
| AU | 2018375566 A1 | 5/2020 | |
| AU | 2019227410 A1 | 8/2020 | |
| BR | PI0712663 A2 | 9/2012 | |
| BR | PI0809369 A2 | 9/2014 | |
| BR | PI0817700 A2 | 3/2015 | |
| BR | 112020010951 A2 | 11/2020 | |
| BR | 112020017895 A2 | 12/2020 | |
| CA | 2210716 A1 | 8/1996 | |
| CA | 2553063 A1 | 2/2007 | |
| CA | 3084507 A1 | 6/2019 | |
| CA | 3090324 A1 | 9/2019 | |
| CN | 101466431 A | 6/2009 | |
| CN | 101678192 A | 3/2010 | |
| CN | 101868269 A | 10/2010 | |
| CN | 102698350 A | 10/2012 | |
| CN | 106620940 A | 5/2017 | |
| CN | 206687973 U | 12/2017 | |
| CN | 111787960 A | 10/2020 | |
| CN | 112402734 A | 2/2021 | |
| CN | 216725486 U | 6/2022 | |
| EP | 0806971 A1 | 11/1997 | |
| EP | 1752182 | 2/2007 | |
| EP | 2019702 A2 | 2/2009 | |
| EP | 2134400 A1 | 12/2009 | |
| EP | 2211942 A2 | 8/2010 | |
| EP | 2514460 A1 | 10/2012 | |
| EP | 3368130 A1 | 9/2018 | |
| EP | 3669924 A1 | 6/2020 | |
| EP | 3717046 A1 | 10/2020 | |
| EP | 3758765 A2 | 1/2021 | |
| ES | 2445793 T3 | 3/2014 | |
| ES | 2793279 T3 | 11/2020 | |
| ES | 2814625 T3 | 3/2021 | |
| JP | 2007500530 A | 1/2007 | |
| JP | 2009538187 A | 11/2009 | |
| JP | 2010522628 A | 7/2010 | |
| JP | 5629571 B2 | 11/2014 | |
| JP | 2021504063 A | 2/2021 | |
| KR | 20200096555 A | 8/2020 | |
| KR | 20200126980 A | 11/2020 | |
| SG | 11201803067 W | 5/2018 | |
| SG | 11202003756 S | 6/2020 | |
| SG | 11202006882X | 9/2020 | |
| TW | I337544 B | 2/2011 | |
| WO | 96/22800 | 8/1996 | |
| WO | WO-9622800 A1 * | 8/1996 | A61M 25/0618 |
| WO | 2007/139740 | 12/2007 | |
| WO | 2008/121829 | 10/2008 | |
| WO | 2009/042583 | 4/2009 | |
| WO | 2013/027355 | 2/2013 | |
| WO | 2017/074679 | 5/2017 | |
| WO | WO-2017214110 A1 * | 12/2017 | A61M 25/0618 |
| WO | 2018165166 A1 | 9/2018 | |
| WO | 2019/108336 | 6/2019 | |
| WO | 2019/168597 | 9/2019 | |
| ZA | 200606361 B | 8/2010 | |

* cited by examiner

INHIBITING FLUID LEAKAGE AND SPLATTER IN CATHETER DEVICES AND SYSTEMS

RELATED APPLICATIONS

This application claims the benefit of U.S. Provisional Application No. 62/949,939, filed Dec. 18, 2019, and entitled INHIBITING FLUID LEAKAGE AND SPLATTER IN CATHETER DEVICES AND SYSTEMS, which is incorporated herein in its entirety.

BACKGROUND

Catheters are commonly used for a variety of infusion therapies. For example, catheters may be used for infusing fluids into a patient such as saline solution, medication, total parenteral nutrition, etc. Catheters may also be used for withdrawing blood from the patient.

A common type of catheter is an over-the-needle peripheral intravenous catheter ("PIVC"). Other common types of catheters include, but are not limited to, peripherally inserted central catheters ("PICC"), central venous catheters ("CVC"), etc.

As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and the introducer needle are typically inserted at a shallow angle through the skin and into a blood vessel of the patient, such as an artery, a vein, or other vasculature of the patient. Once the PIVC has been properly placed within the blood vessel, the introducer needle may be withdrawn and the PIVC may be secured within the blood vessel by securing a catheter adapter (coupled with the PIVC) to the skin of the patient with dressing.

However, fluid leakage (e.g., blood, medications, saline solutions, etc.) can occur during insertion of a catheter, such as a PIVC. For example, blood leakage may occur during insertion of a Cathena™ catheter while the introducer needle is parked within the septum of the catheter adapter. In this configuration, blood may be able to leak out of the catheter adapter through a small space or gap formed between the septum and the introducer needle when the introducer needle is parked within the septum. This leaked blood may then flow into the needle tip shield through the needle passageway of the needle tip shield. Once blood has entered into the needle tip shield, the blood may then proceed to leak out of the needle tip shield through an opening on the needle tip shield that receives a V-Clip safety mechanism. Moreover, blood may splatter out of the opening when the V-Clip fires to trap the needle tip within the needle tip. Accordingly, improved devices, systems, and methods for restricting fluid splatter and leakage into and/or out of the needle tip shield would be desirable.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to catheter devices and systems. The various catheter devices and systems of the present disclosure have been developed in response to the present state of the art, and in particular, in response to the problems and needs in the art that have not yet been fully solved by currently available catheter devices and systems for inhibiting fluid leakage and splatter during catheter insertion.

In some embodiments, a needle tip shield may include a needle passageway, a tip shield interior space, and a fluid restriction member. The needle passageway may be formed through the needle tip shield and may receive a needle therethrough. The tip shield interior space may receive a needle block therein and the tip shield interior space may include an opening for inserting the needle block into the tip shield interior space. The fluid restriction member may be configured to restrict fluid leakage into and/or out of the needle tip shield. The fluid restriction member may be selected from the group consisting of: (1) a fluid impedance member located adjacent the needle passageway that may impede fluid from entering into the needle tip shield through the needle passageway; (2) a fluid retention member that may retain fluid within the tip shield interior space; and (3) an anti-splatter member that may inhibit fluid splatter when the needle block moves from an open position to a closed position within the tip shield interior space.

In some embodiments of the needle tip shield, the selection may include the fluid impedance member. In some embodiments, the fluid impedance member may include at least one of: a sponge, an absorbent plug, a foam, a wicking material, a hydrogel, a high viscosity silicone lube, an O-ring, a compliant septum, a membrane, and a tip shield nose that is shaped to impede fluid from entering into the needle tip shield through the needle passageway.

In some embodiments of the needle tip shield, the selection may include the fluid retention member. In some embodiments, the fluid retention member may include at least one of a cover placed over the opening to retain fluid within the tip shield interior space, and an absorbent material placed within the tip shield interior space to retain fluid within the tip shield interior space.

In some embodiments of the needle tip shield, the selection may include the anti-splatter member. In some embodiments, the anti-splatter member may include at least one of a damping member and a shock absorbing material. In some embodiments, the needle block may include a V-Clip that is movable between the open position and the closed position, such that: (1) in the open position, the V-Clip allows a needle to advance distally through the needle passageway; (2) in the closed position, the V-Clip prevents the needle from advancing distally through the needle passageway; (3) the damping member may be coupled to the V-Clip to slow movement of the V-Clip as it moves from the open position to the closed position; and (4) the shock absorbing material may be placed within the tip shield interior space adjacent the V-Clip to slow movement of the V-Clip as it moves from the open position to the closed position.

In some embodiments of the needle tip shield, the damping member may include a visco-elastic material.

In some embodiments of the needle tip shield, the damping member may further include a stiffening member coupled to the visco-elastic material.

In some embodiments, a needle tip shield may impede fluid from entering into the needle tip shield, and may include a needle passageway and a fluid impedance member. The needle passageway may be formed through the needle tip shield and may receive a needle therethrough. The fluid impedance member may be located adjacent the needle passageway and may impede fluid from entering into the needle tip shield through the needle passageway.

In some embodiments of the needle tip shield, the fluid impedance member may include an absorbent material including at least one of: a sponge, an absorbent plug, a foam, and a wicking material.

In some embodiments of the needle tip shield, the fluid impedance member may include a viscous material including at least one of a hydrogel and a high viscosity silicone lube.

In some embodiments of the needle tip shield, the fluid impedance member may include a compliant material including at least one of an O-ring and a compliant septum.

In some embodiments of the needle tip shield, the fluid impedance member may include a tip shield nose that is shaped to impede fluid from entering into the needle tip shield.

In some embodiments, the needle tip shield may further include a recess adjacent the needle passageway that receives the fluid impedance member therein.

In some embodiments, the needle tip shield may further include a membrane coupled to the needle tip shield adjacent the needle passageway that impedes fluid from entering into the needle tip shield.

In some embodiments, a needle tip shield that may retain fluid within the needle tip shield, and may include a needle passageway, a tip shield interior space, and a fluid retention member. The needle passageway may be formed through the needle tip shield and may receive a needle therethrough. The tip shield interior space may receive a needle block therein, and the tip shield interior space may include an opening for inserting the needle block into the tip shield interior space. The fluid retention member may retain fluid within the tip shield interior space.

In some embodiments of the needle tip shield, the fluid retention member may include a cover placed over the opening to retain fluid within the tip shield interior space.

In some embodiments of the needle tip shield, the cover may include at least one of: a tape, a heat seal material, a thin film, and a plastic cover.

In some embodiments of the needle tip shield, the cover may be coupled to the needle tip shield with at least one of: an adhesive, a snap feature, an interference feature, a heat seal material, a glue, and sonic welding.

In some embodiments of the needle tip shield, the fluid retention member may include at least one of: a sponge, a foam, an absorbent material, a wicking material, and a clotting material.

In some embodiments of the needle tip shield, the fluid retention member may be placed within the tip shield interior space.

In some embodiments of the needle tip shield, the fluid retention member may be coupled to the needle block.

It is to be understood that both the foregoing general description and the following detailed description are exemplary and explanatory and are not restrictive of the embodiments of the present disclosure, as claimed. It should be understood that the various embodiments of the present disclosure are not limited to the arrangements and instrumentality shown in the drawings. It should also be understood that the embodiments of the present disclosure may be combined, or that other embodiments may be utilized and that structural changes, unless so claimed, may be made without departing from the spirit or scope of the various embodiments of the present disclosure. The following detailed description is, therefore, not to be taken in a limiting sense.

BRIEF DESCRIPTION OF THE DRAWINGS

Example embodiments will be described and explained with additional specificity and detail through the use of the accompanying drawings in which.

It is to be understood that the Figures are for purposes of illustrating the concepts of the present disclosure and may not be drawn to scale. Furthermore, the Figures illustrate exemplary embodiments and do not represent limitations to the scope of the present disclosure.

DESCRIPTION OF EMBODIMENTS

Exemplary embodiments of the present disclosure will be best understood by reference to the Figures, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and systems, as represented in the Figures, is not intended to limit the scope of the present disclosure, as claimed in this or any other application claiming priority to this application, but is merely representative of exemplary embodiments of the present disclosure.

Figure 1:
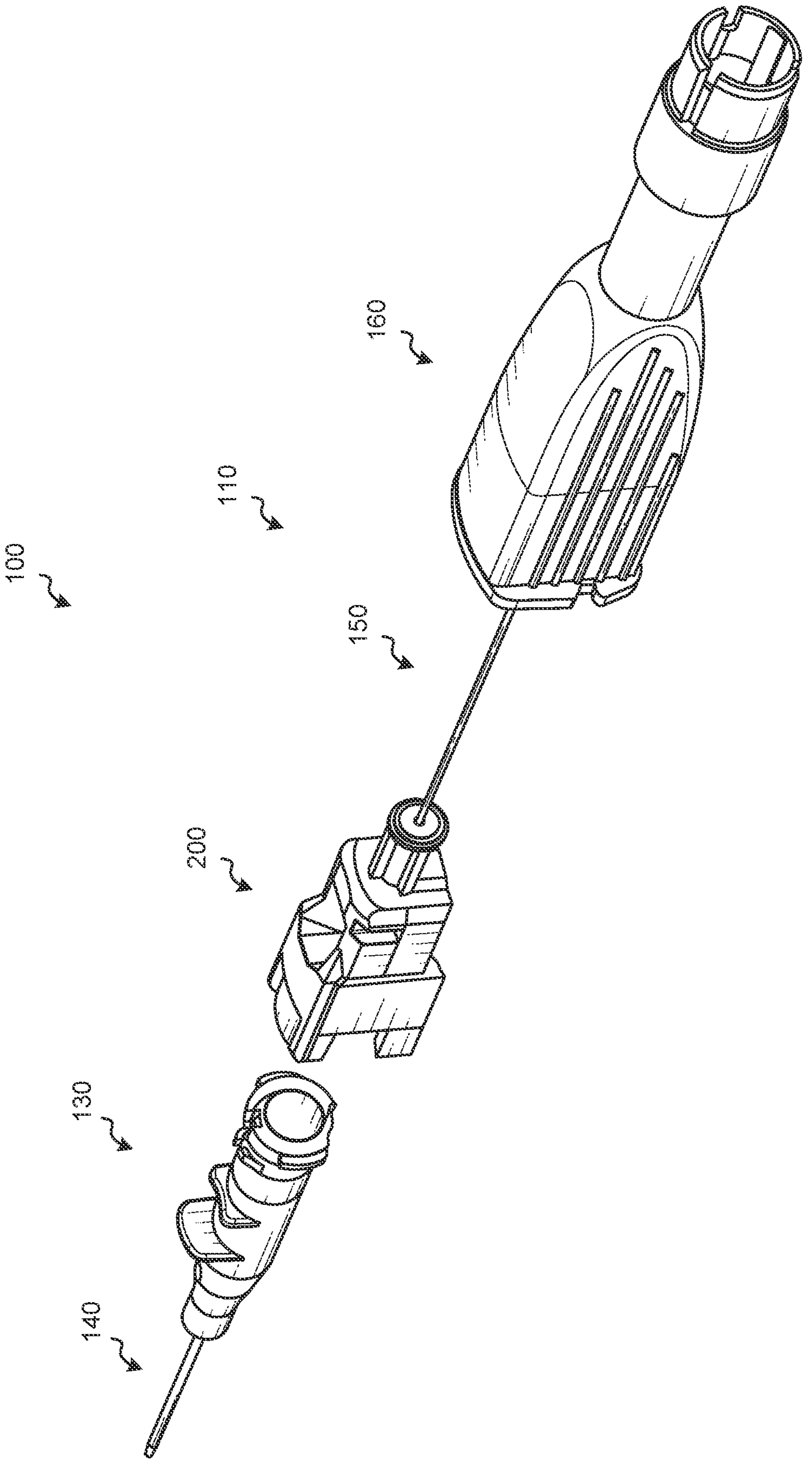
FIG. 1 is an exploded view of an example catheter system that utilizes a needle tip shield, according to some embodiments.

FIG. 1 illustrates an exploded view of a catheter system 100 that may be utilized with the teachings of the present disclosure, according to some embodiments. However, it will be understood that the teachings of the present disclosure can be utilized with any catheter system known in the art. The catheter system 100 may include a needle assembly 110 including a needle 150 coupled to a needle hub 160, a needle tip shield 200, a catheter adapter body 130, and a catheter 140 coupled to a distal end of the catheter adapter body 130.

Figure 2B:
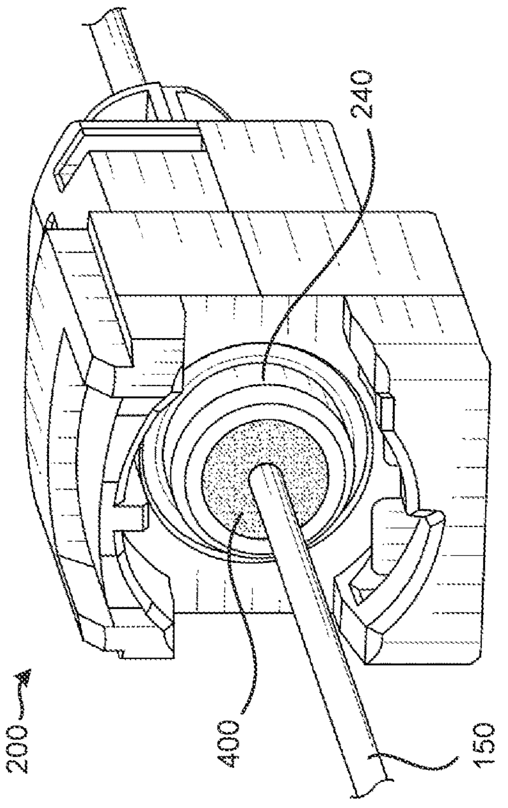
FIG. 2B shows the needle tip shield of FIG. 2A coupled with a fluid impedance member.
Figure 2A:
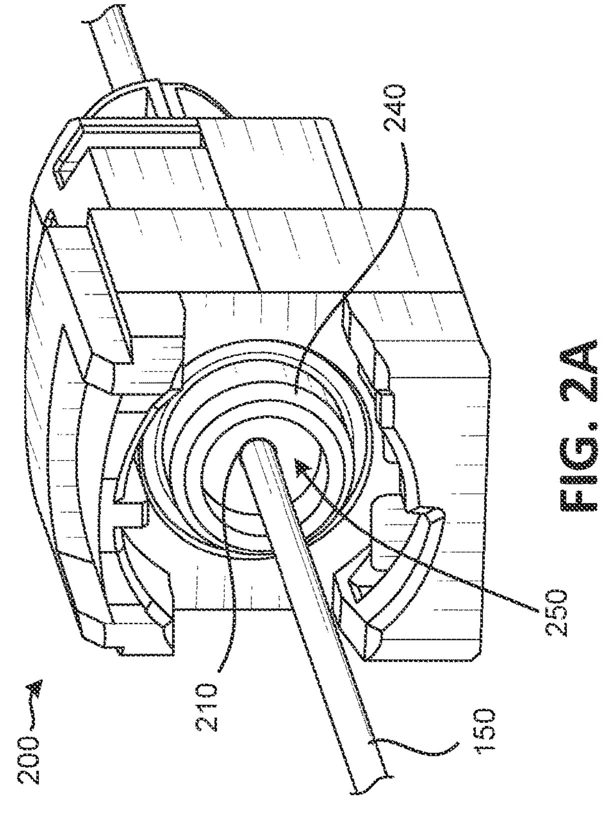
FIG. 2A is a front perspective view of the needle tip shield of FIG. 1.
Figure 2C:
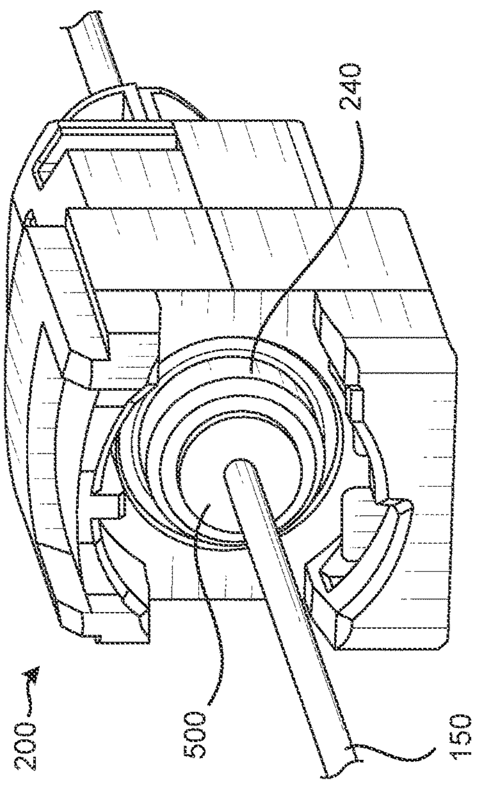
FIG. 2C shows the needle tip shield of FIG. 2A coupled with a membrane.

FIGS. 2A-2C illustrate various views of the needle tip shield 200 of FIG. 1. Specifically, FIG. 2A is a front perspective view of the needle tip shield 200 of FIG. 1; FIG. 2B shows the needle tip shield 200 of FIG. 2A coupled with a fluid impedance member 400; and FIG. 2C shows the needle tip shield 200 of FIG. 2A coupled with a membrane 500.

The needle tip shield 200 may include a needle passageway 210 formed through the needle tip shield 200. The needle passageway 210 may be configured to slidably receive the needle 150 therethrough. In some embodiments, a diameter of the needle 150 may be slightly smaller than a diameter of the needle passageway 210 such that a small gap may exist between the needle 150 and the needle passageway 210 that may allow fluid to flow therethrough. In some embodiments, the needle tip shield 200 may also include a tip shield nose 240. In some embodiments, the tip shield nose 240 may encircle (or otherwise surround) the needle passageway 210 and/or project distally away from the needle passageway 210. In some embodiments, a recess 250 may be formed in the tip shield nose 240.

In some embodiments, a fluid impedance member 400 may be located adjacent the needle passageway 210. The fluid impedance member 400 may impede/prevent fluid from entering into the needle tip shield 200 through the needle passageway 210 by creating a seal around the needle 150. Preventing and/or decreasing blood flow into the needle tip shield 200 can eliminate subsequent blood leakage out of the needle tip shield 200 and/or increase the length of time before blood leakage occurs from the needle tip shield 200.

In some embodiments, the fluid impedance member 400 may be placed within the recess 250 that is formed in the tip shield nose 240, as shown in FIG. 2B.

In some embodiments, the fluid impedance member 400 may include an absorbent material.

In some embodiments, the absorbent material may, but not be limited to, a sponge, an absorbent plug, a foam, a wicking material (e.g., a cellulous, gelatin, micro spun mesh, PEG material, etc.), a clotting material, etc.

In some embodiments, the fluid impedance member 400 may include a viscous material.

In some embodiments, the viscous material may include, but not be limited to, a hydrogel, a high viscosity silicone lube, etc.

In some embodiments, the fluid impedance member 400 may include a compliant material.

In some embodiments, the compliant material may include an O-ring, a compliant septum, etc.

In some embodiments, the fluid impedance member 400 may include a membrane 500 located distal the needle passageway 210. The membrane 500 may impede/prevent fluid from entering into the needle tip shield 200.

In some embodiments, the membrane 500 may be coupled to the needle tip shield 200 adjacent the needle passageway.

In some embodiments, the membrane 500 may be coupled to the tip shield nose 240.

In some embodiments, the membrane 500 may be coupled to a distal end of the tip shield nose 240, as is shown in FIG. 2C.

In some embodiments, the membrane 500 may include a needle aperture (not shown) for receiving the needle 150 therethrough.

In some embodiments, the membrane 500 may include a penetrable membrane. In these embodiments the needle 150 may penetrate the membrane 500 as the needle 150 is inserted through the needle tip shield 200.

In some embodiments, the membrane 500 (and/or the fluid impedance member 400) may be coupled to the needle tip shield 200 (and/or coupled to the tip shield nose 240) by any suitable means including, but not limited to, an adhesive, a glue, a snap feature, an interference feature, a heat seal material, sonic welding, etc.

In some embodiments, the tip shield nose 240 may be shaped to impede fluid from entering into the needle tip shield 200. For example, the tip shield nose 240 may include a shape similar to a tip shield nose of a Venflon™ catheter (not shown), which has a revolver-shaped nose design.

Figure 3B:
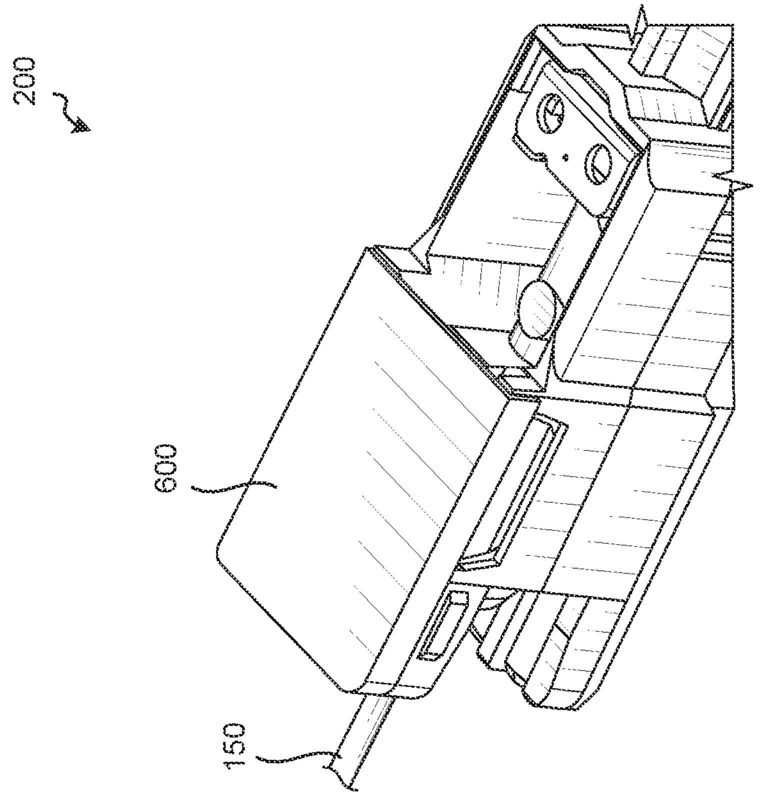
FIG. 3B shows the needle tip shield of FIG. 3A coupled with a cover.
Figure 3A:
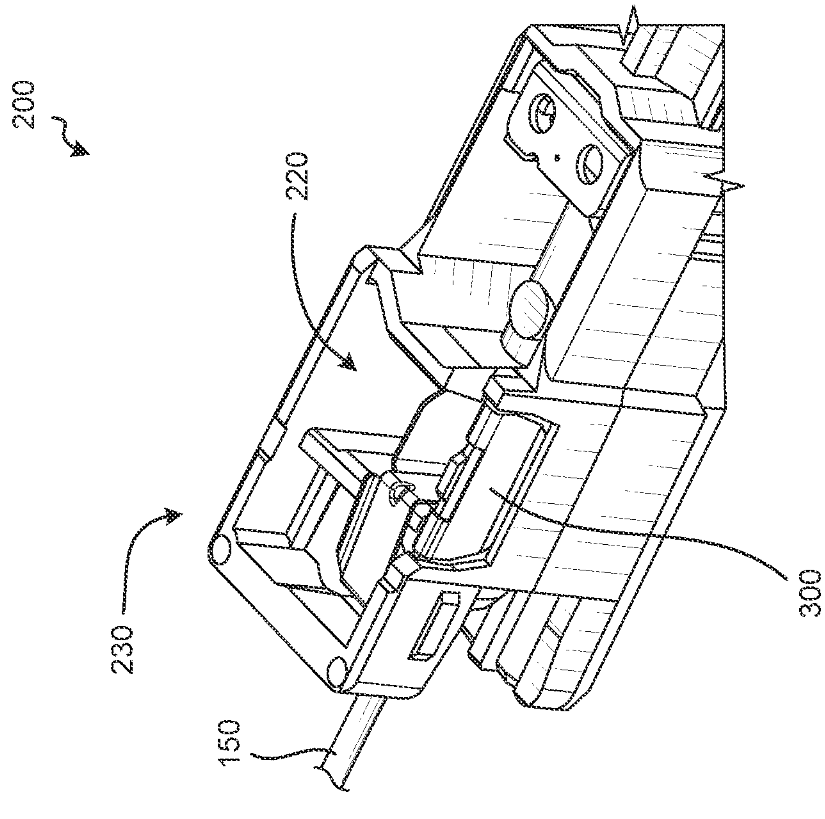
FIG. 3A is a bottom perspective view of the needle tip shield of FIG. 1.
Figure 4:
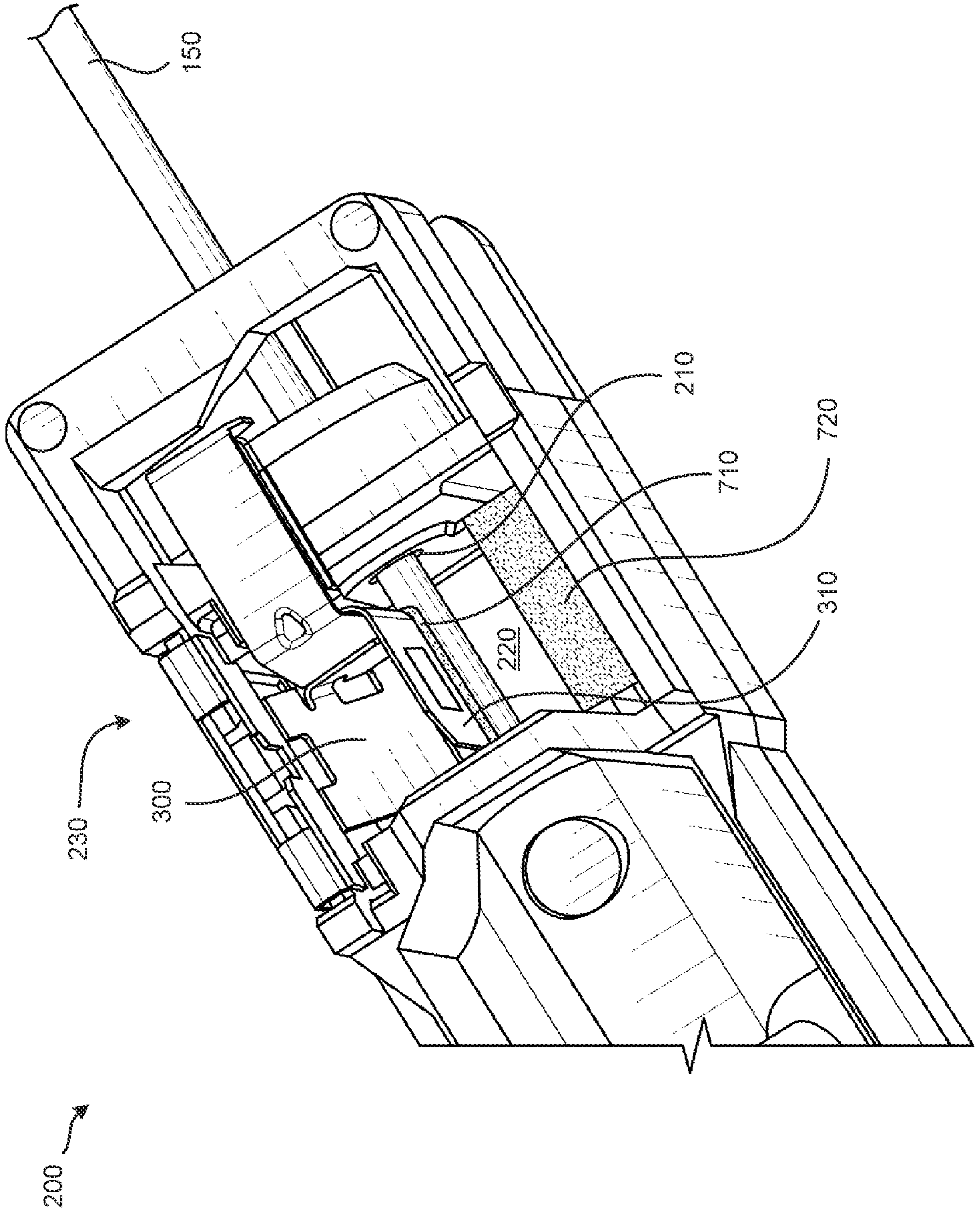
FIG. 4 is a bottom perspective view of the needle tip shield of FIG. 1 with an absorbent material placed therein.

FIGS. 3A-4 illustrate various views of the needle tip shield 200 of FIG. 1 in combination with a fluid retention member that may retain fluid within the needle tip shield 200. Specifically, FIG. 3A is a bottom perspective view of the needle tip shield 200 of FIG. 1; FIG. 3B shows the needle tip shield 200 of FIG. 3A coupled with a fluid retention member including a cover 600; and FIG. 4 shows a bottom perspective view of the needle tip shield 200 of FIG. 1 with one or more fluid retention members including absorbent material placed within the needle tip shield 200.

The needle tip shield 200 may include a tip shield interior space 220 configured to receive a needle block therein, such as a V-Clip 300 (as one non-limiting example). The tip shield interior space 220 may also include an opening 230 for inserting the V-Clip 300 into the tip shield interior space 220.

In some embodiments, the fluid retention member includes the cover 600. The cover 600 may be placed over the opening 230 to retain fluid within the tip shield interior space 220, as shown in FIG. 3B.

In some embodiments, the cover 600 may include any suitable material including, but not limited to, a tape, a heat seal material, a thin film, a plastic cover, etc.

In some embodiments, the cover 600 may be coupled to the needle tip shield 200 over the opening 230 by any suitable means including, but not limited to, an adhesive, a glue, a snap feature, an interference feature, a heat seal material, sonic welding, etc.

In some embodiments, the fluid retention member may include an absorbent material.

In some embodiments, a first absorbent material 710 may be coupled to the V-Clip 300, or other needle block, as shown in FIG. 4.

In some embodiments, the first absorbent material 710 may be coupled to a surface 310 of the V-Clip 300 adjacent the needle 150. In this manner, the first absorbent material 710 may absorb fluid from the needle 150 as the needle 150 slides past the first absorbent material 710.

In some embodiments, a second absorbent material 720 may be placed within the tip shield interior space 220 and/or coupled to the needle tip shield 200, as shown in FIG. 4. In this manner, the second absorbent material 720 may absorb fluid within the tip shield interior space 220 that may come into contact with the second absorbent material 720. However, it will also be understood that any number of absorbent materials may be placed within the tip shield interior space 220 and/or coupled to any part of the needle tip shield 200 and/or V-Clip 300 to help retain fluid within the needle tip shield 200.

In some embodiments, the first absorbent material 710 and/or the second absorbent material 720 may each include any suitable material including, but not limited to, a sponge, a foam, a wicking material (e.g., a cellulous, gelatin, micro spun mesh, PEG material, etc.), a clotting material, etc.

Figure 5B:
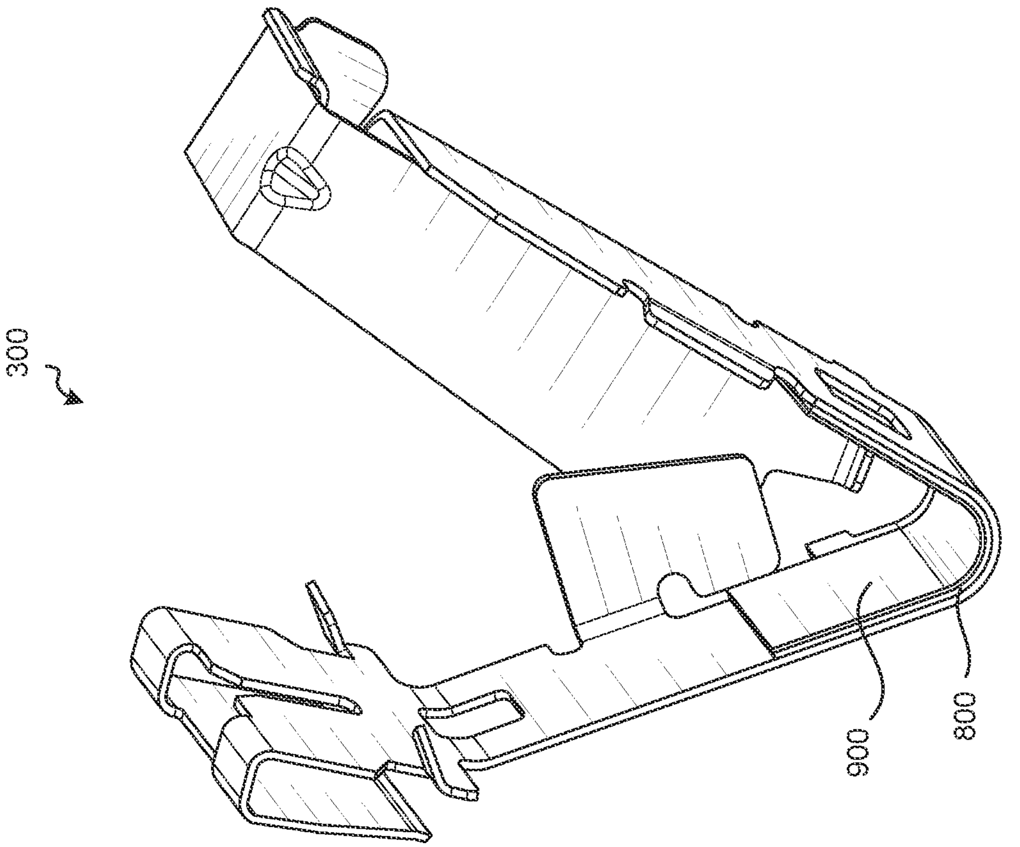
FIG. 5B shows the V-Clip of FIG. 5A with a stiffening member coupled over the damping member.
Figure 5A:
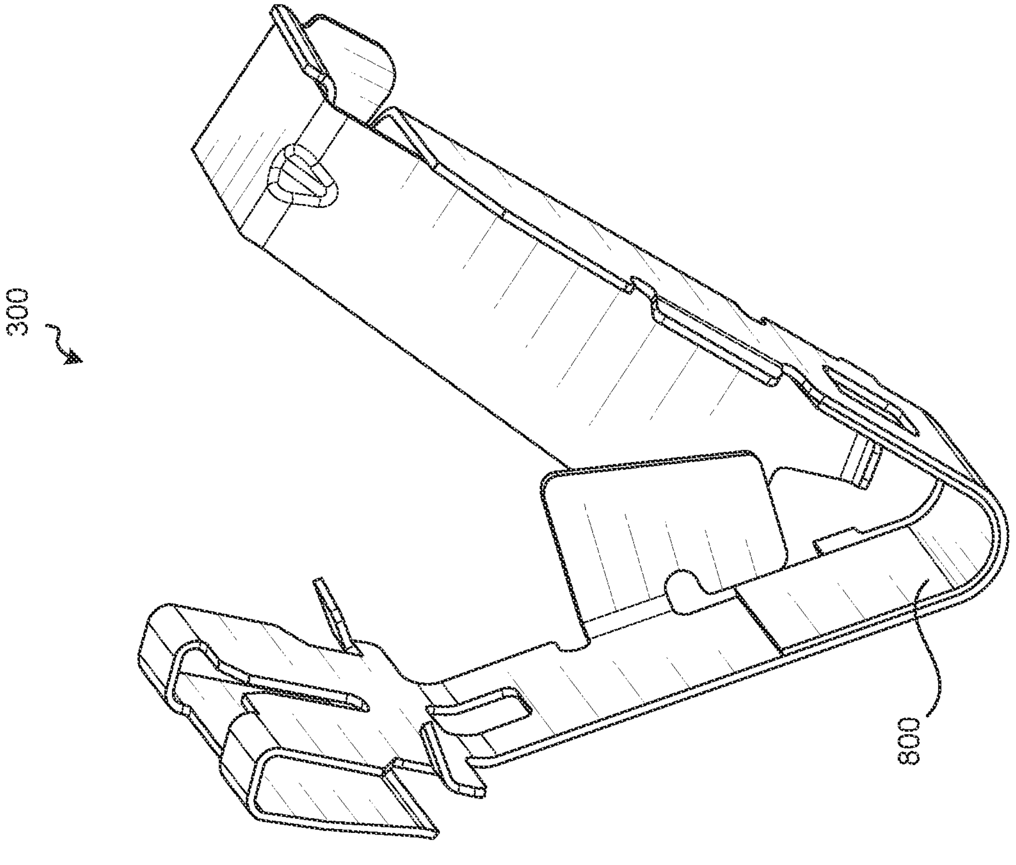
FIG. 5A is a perspective view of a V-Clip with a damping member coupled thereto.

FIGS. 5A and 5B illustrate various views of the V-Clip 300 coupled with an anti-splatter member and removed from the needle tip shield 200 of FIG. 1. Specifically, FIG. 5A is a perspective view of the V-Clip 300 with an anti-splatter member including a damping member 800, and FIG. 5B shows the V-Clip 300 of FIG. 5A with an anti-splatter member including the damping member 800 and a stiffening member 900 coupled over the damping member 800 to form a constrained-layer damping member.

Each of these V-Clip 300 designs may inhibit fluid splatter when the V-Clip 300 "fires" or "snaps closed" within the tip shield interior space 220 by slowing down the V-Clip 300 when it fires. For example, the V-Clip 300 may be movable between an open position and a closed position. In the open position, the V-Clip 300 may allow the needle 150 to advance distally through the needle passageway 210. In the closed position, the V-Clip 300 may prevent the needle 150 from advancing distally through the needle passageway 210. Thus, in the closed position, the V-Clip 300 may trap the tip of the needle 150 within the needle tip shield 200 as a safety mechanism. The V-Clip 300 may fire into the closed position when the needle 150 is pulled far enough proximally to allow the V-Clip 300 (which may be resilient) to fire and move toward the closed position.

In some embodiments, the anti-splatter member includes the damping member 800 coupled to the V-Clip 300, as shown in FIG. 5A, in order to slow movement of the V-Clip 300 as it moves from the open position to the closed position.

In some embodiments, the damping member 800 includes a visco-elastic material that may act to slow movement of the V-Clip 300 as it moves from the open position to the closed position.

In some embodiments, the anti-splatter member includes the damping member 800 in combination with the stiffening member 900, which may be coupled over the damping member 800 in order to form a constrained-layer damping member.

In some embodiments, the stiffening member 900 may act to increase visco-elastic forces that may be associated with the visco-elastic material in order to further slow movement of the V-Clip 300 as it moves from the open position to the closed position.

In some embodiments, the stiffening member 900 may include any suitable material including, but not limited to, metal, plastic, tape, fabric, etc.

In some embodiments, the damping member 800 and/or the stiffening member 900 may be coupled to the V-Clip 300 and/or to each other via any suitable means including, but not limited to, an adhesive, a glue, a snap feature, an interference feature, a heat seal material, sonic welding, etc.

Figure 6:
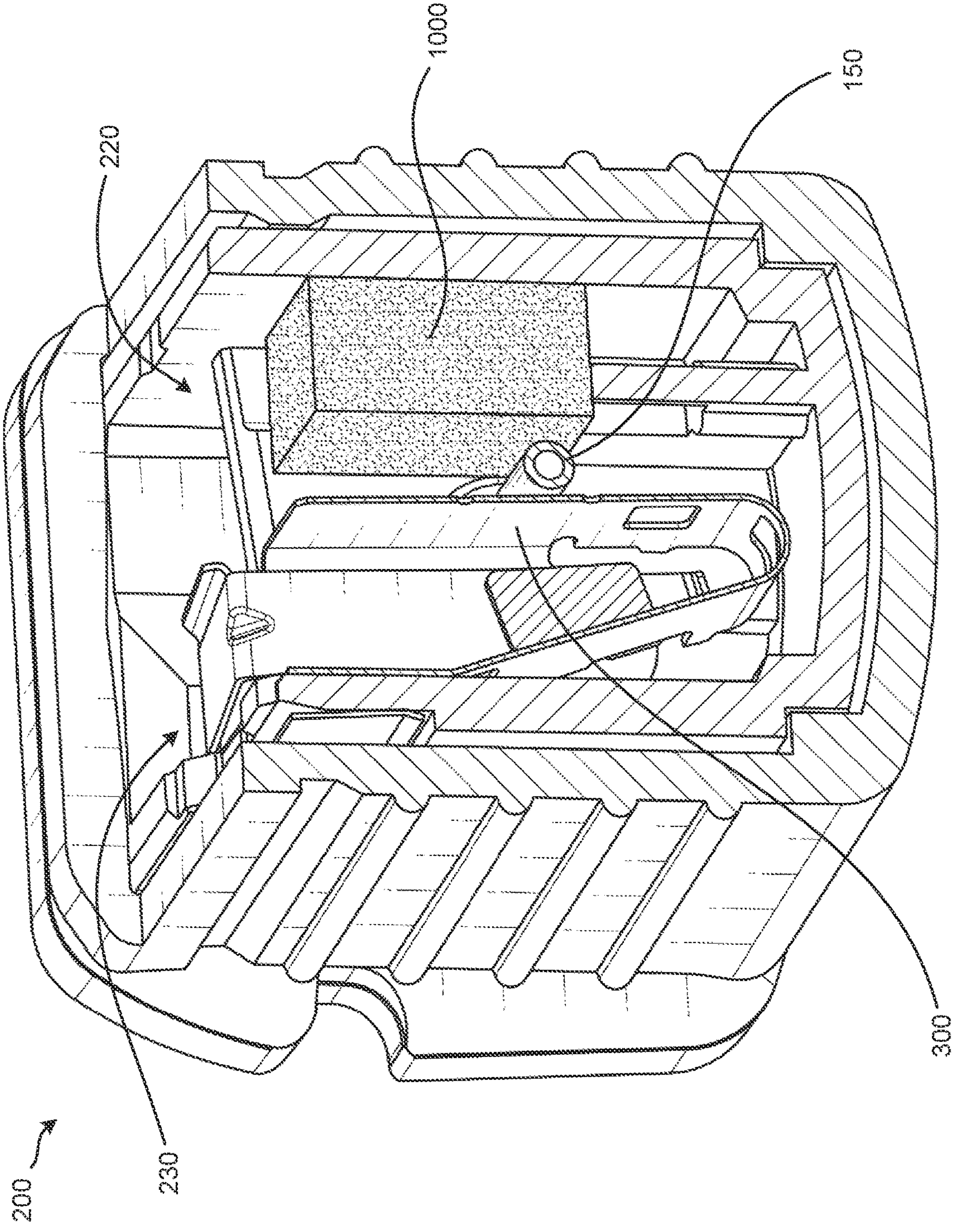
FIG. 6 is a cross-sectional view of the needle tip shield of FIG. 1 with a shock absorbing material placed therein.

FIG. 6 shows a cross-sectional view of the needle tip shield 200 of FIG. 1 with an anti-splatter member placed within the tip shield interior space 220.

In some embodiments, the anti-splatter member may include a shock absorbing material 1000 placed adjacent the V-Clip 300. The shock absorbing material 1000 may act to slow movement of the V-Clip 300 as it moves from the open position to the closed position and prevent/reduce fluid splatter.

In some embodiments, the shock absorbing material 1000 may include any suitable material including, but not limited to, a foam, a sponge, an absorbent material, a wicking material (e.g., a cellulous, gelatin, micro spun mesh, PEG material, etc.), a clotting material, etc.

It will be understood that any/all of the fluid restriction members described herein may be utilized alone and/or in combination with any/all of the other fluid restriction members that are described herein. For example, in some embodiments the needle tip shield 200 may generally include one or more of the fluid restriction members described herein, each of which may be configured to restrict fluid splatter and/or fluid leakage into and/or out of the needle tip shield 200. In some embodiments, the fluid restriction member may be selected from the group consisting of: (1) a fluid impedance member located adjacent the needle passageway 210 that impedes fluid from entering into the needle tip shield 200 through the needle passageway 210 (e.g., see FIGS. 2A-2C); (2) a fluid retention member that retains fluid within the tip shield interior space 220 (e.g., see FIGS. 3A-4); and (3) an anti-splatter member that inhibits fluid splatter when the V-Clip 300 or needle block moves from the open position to the closed position within the tip shield interior space 220 (e.g., see FIGS. 5A-6).

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. It is to be understood that any of the embodiments of the present disclosure, or any portion(s) of any of the embodiments of the present disclosure, may be combined together in any number of different ways.

Similarly, it should be appreciated that in the above description of embodiments, various features are sometimes grouped together in a single embodiment, Figure, or description thereof for the purpose of streamlining the disclosure. This disclosure format, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Description Of Embodiments are hereby expressly incorporated into this Description Of Embodiments, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

As defined herein, "substantially equal to" means "equal to," or within about a + or −10% relative variance from one another.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the Figures, the Figures are not necessarily drawn to scale unless specifically indicated.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the apparatus and systems disclosed herein.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A needle tip shield comprising:

a needle passageway formed through the needle tip shield for receiving a needle therethrough;

a tip shield interior space that receives a needle block therein, wherein the needle block comprises a V-clip, the tip shield interior space comprising an opening for inserting the needle block into the tip shield interior space; and a fluid restriction member configured to restrict fluid leakage into and/or out of the needle tip shield, wherein the fluid restriction member comprises an anti-splatter member that inhibits fluid splatter when the needle block moves from an open position to a closed position within the tip shield interior space, wherein the anti-splatter member comprises a damping member and a stiffening member coupled to an inner surface of a V-portion of the V-clip, wherein the damping member is disposed in between the stiffening member and the V-clip.

2. The needle tip shield of claim 1, wherein:

the V-clip is movable between the open position and the closed position, such that:

in the open position, the V-clip allows the needle to advance distally through the needle passageway;

in the closed position, the V-clip prevents the needle from advancing distally through the needle passageway;

the damping member is coupled to the V-clip to slow movement of the V-clip as it moves from the open position to the closed position.

3. The needle tip shield of claim 2, wherein the damping member comprises a visco-elastic material.

4. The needle tip shield of claim 3, wherein the stiffening member is coupled to the visco-elastic material.

* * * * *